US006616915B1

(12) United States Patent
Griesbach et al.

(10) Patent No.: US 6,616,915 B1
(45) Date of Patent: Sep. 9, 2003

(54) USE OF SURFACTANT MIXTURES

(75) Inventors: Ute Griesbach, Dusseldorf (DE); Rolf Wachter, Dusseldorf (DE); Bernd Fabry, Korschenbroich (DE); Rolf E. Engstad, Tromso (NO)

(73) Assignee: Biotec ASA, Tromso (NO)

( * ) Notice: Subject to any disclaimer, the term of this patent is extended or adjusted under 35 U.S.C. 154(b) by 0 days.

(21) Appl. No.: 09/937,012

(22) PCT Filed: Mar. 3, 2000

(86) PCT No.: PCT/EP00/01828

§ 371 (c)(1),
(2), (4) Date: Jan. 22, 2002

(87) PCT Pub. No.: WO00/54739

PCT Pub. Date: Sep. 21, 2000

(30) Foreign Application Priority Data

Mar. 12, 1999 (DE) .......................... 199 11 055

(51) Int. Cl.$^7$ .................................................. A61K 7/16
(52) U.S. Cl. .......................................... 424/49; 424/48
(58) Field of Search ...................... 424/48–58

(56) References Cited

U.S. PATENT DOCUMENTS

| 3,931,398 A | | 1/1976 | Gaffar et al. | |
| 4,340,673 A | * | 7/1982 | Stoudt et al. | 435/97 |
| 4,512,968 A | * | 4/1985 | Komiyama et al. | 424/49 |
| 5,711,938 A | * | 1/1998 | Larm | 424/49 |
| 5,814,341 A | * | 9/1998 | Fankhauser et al. | 424/493 |
| 5,869,029 A | * | 2/1999 | Graff-Andersen et al. | 424/52 |
| 6,159,459 A | * | 12/2000 | Hunter et al. | 424/49 |
| 6,162,449 A | * | 12/2000 | Maier et al. | 424/401 |
| 6,258,342 B1 | * | 7/2001 | Harcum et al. | 424/401 |
| 6,369,217 B1 | * | 4/2002 | Maier et al. | |

FOREIGN PATENT DOCUMENTS

| GB | 2176795 | | 1/1987 |
| JP | 10287536 | | 10/1998 |
| WO | WO 9523582 | | 9/1995 |
| WO | WO 9530022 | | 11/1995 |
| WO | WO 9530403 | | 11/1995 |
| WO | 96/34608 | * | 11/1996 |
| WO | WO 9932073 | | 7/1999 |

* cited by examiner

*Primary Examiner*—Shep K. Rose
(74) *Attorney, Agent, or Firm*—Ladas & Parry

(57) ABSTRACT

The invention relates to the use of surfactant mixtures, comprising (a) anionic and/or nonionic surfactants and (b) water soluble β-(1,3) glucans, which are substantially free of β-(1,6) links. Said mixtures are used to produce oral hygiene and dental hygiene products in particulars, toothpastes. The preparations are characterized in that the mucous membranes in the mouth have a particularly high degree of tolerability with regard thereto, by exhibiting exceptional foaming properties and a stable distribution of the abrasive substances.

11 Claims, No Drawings

USE OF SURFACTANT MIXTURES

FIELD OF THE INVENTION

The invention resides in the area of mouth and teeth hygiene and concerns the use of preparations containing anionic and/or nonionic surfactants and selected glucans for producing oral hygiene and dental hygiene products as well as toothpastes with a defined composition.

The term oral hygiene and dental hygiene products is of one skilled in the art understood to be a liquid preparation, which as mouthwash disinfects the area of the mouth and throat, secondly are therewith understood paste or since a time back also tooth cleaning agents in the form of gels. These preparations are according to the requirements of their users—especially by small injuries in mouth and throat areas—not to lead to irritations. In the case of tooth care products the additional requirements are that the preparations must have a strong foam, a neutral taste and active cleaning abilities.

PRIOR ART

The term oral hygiene and dental hygiene products is of one skilled in the art understood to be a liquid preparation, which as mouthwash desinfects the area of the mouth and throut, secondly are therewith understood paste or since a time back also tooth cleaning agents in the form of gels. These preparations are according to the requirements of the users especially mucosa compatible, in order to—especially by small injuries in mouth and throut areas—not to lead to irritations. In the case of tooth care products the additional requirements are that the preparations must have a strong foam, a neutral taste and active cleaning abilities.

In this connection reference is for example made to the German patent application DE-A1 4406748 (Henkel), from which oral hygiene and dental hygiene products are known where the surfactant component mainly is made up of anionic surfactants of the type of monoglyceride sulphate and nonionic surfactants of the type of alkylglucosides. However, a drawback connected with these agents of the known art is that the compatibility with the oral mucosa, foam stability and cleaning efficiency is not completely satisfactory. Moreover, a special problem is to disperse abrasive ingredients in toothpastes and especially tooth gels, so that there will be no agglomeration or separation even at temperature storage.

In this connection reference is made to the international patent application WO 96/34608 (Colgate) where the use of β-glucans against xerostomia is known. The object of U.S. Pat. No. 3,931,398 (Colgate) is the subcutaneous administration of glucans in the vicinity of the oral cavity to combat caries. In the German patent application DE-A1 3621303 (FMC) gels based on β-1,3-glucans are suggested, which for example are made from agrobakterium and can be used in toothpastes. Finally, U.S. Pat. No. 4,340,673 (Merck) describes that special glucans with molecular weights above 500,000 can be used for combatting plaque.

Accordingly, the subject of the invention has consisted in alleviating the above mentioned disadvantages of the known art, by providing especially mouth-and tooth care products, especially toothpastes, which at the same time are caracterised by an optimal compatibility with the oral mucosa, foam stability and cleaning efficiency, immune stimulating and antimicrobial properties as well as especially a stable distribution of the abrasive bodies.

DESCRIPTION OF THE INVENTION

The object of the invention is the use of surfactant mixtures, containing (a) anionic and/or nonionic surfactants and
(b) water soluble β-(1,3) glucans, which are substantially free of β-(1,6) linkages, for the manufacture of oral hygiene and dental hygiene products, especially toothpastes Surprisingly it was found that addition of only small amounts of water soluble β-(1,3) glucans, which are substantially free of unwanted (1,6) linkages, to known mouth or tooth care agents with a content of common anionic and/or nonionic surfactants not only improve their compatibility with the oral mucosa, but also supports the plaque removal, stabilize the foam and especially give a homogeneous and storage stable distribution of abrasive substances. The invention comprises the perception that the preparations further have antimicrobial effect and stimulate the immune system. By "agents" it is in connection with the invention therefore only meant toothpastes and toothgels, but also aqueous alcohol based mouthwash as well as chewing gums.

ANIONIC AND/OR NONIONIC SURFACTANTS

Typical examples of anionic surfactants are soaps, alkylbenzene sulphonates, alkane sulphonates, olefine sulphonates, alkylether sulphonates, glycerolether sulphonates, α-methylester sulphonates, sulphofatty acids, alkyl sulphates, fatty alcohol ether sulphates, glycerol ether sulphates, mixed hydroxy ether sulphates, monoglyceride (ether) sulphates, fatty acid amide (ether) sulphates, mono- and dialkyl sulphosuccinates, mono- and dialkyl sulfosuccinamates, sulpho triglycerides, amido soaps, ether carboxylic acids and their salts, fatty acid isethionates, fatty acid sarcosinates, fatty acid taurides, N-acylamino acids such as for example acyl lactylate, acyl tartrate, acyl glutamate and acyl aspartate, alkyl oligoglucoside sulphate, protein fatty acid condensate (especially plant products based on wheat) and alkyl (ether) phosphate. If the anionic surfactants contain polyglycol ether chains, these could show a conventional, but preferably a narrow homologue distribution. Typical examples of nonionic surfactants are fatty alcohol polyglycol ethers, alkylphenol polyglycol ethers, fatty acid polyglycol esters, fatty acid amide polyglycol ethers, fatty amino polyglycol ethers, alkoxylated triglycerides, mixed ethers, respectively mixed formals, possibly partially oxididized alk(en)yl oligoglycosides, respectively glucoronic acid derivatives, fatty acid-N-alkylglucamides, protein hydrolysates (especially plant products based on wheat), polyol fatty acid esters, sugar esters, sorbitan esters, polysorbates and amine oxides. Provided that the nonionic surfactants contain polyglycolether chains, these can show a conventional, but preferably a narrow distribution of homologues. Based on application technology reasons—especially compatibility with the oral mucosa and foaming ability—the use of alkyl sulphates, alkyl ether sulphates, monoglyceride (ether) sulphates, olefine sulphonates and alkyl and/or alkenyl oligoglycosides as well as their mixtures is preferable, and they can be used as water containing pastes, preferably, however, as water free powders or granulates, which can be obtained for example by the Flash-Dryer or by the SKET procedure.

Alkyl Sulphates and Alkyl Ether Sulphates

Alkyl sulphates and alkyl ether sulphates, which are of interest as components (a), are known anionic surfactants, which in industrial scale are produced by sulphation of primary alcohols—preferably fatty alcohols or oxo alcohols—or their ethylene oxide addition products, and thereafter neutralisation of the resulting sulphuric acid half ester with bases. Preferably they have the following formula (I), $$R^1O(CH_2CH_2O)_nSO_3X \quad (I)$$

where $R^1$ represents a linear or branched alkyl residue with 6 to 22 carbon atoms, n represents 0 or a number from 1 to 10 and X represents an alkali or alkaline earth metal, ammonium, alkyl ammonium, alkanol ammonium or glucammonium. Typical examples are the suphation products of caprone alcohol, capryl alcohol, 2-ethylhexyl alcohol, caprin alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their technal mixtures, which e.g. are obtained by the high pressure hydrogenation of methyl esters of technical quality based on fats and oils or aldehydes of Roelen's oxo synthesis and as fraction of monomers by the dimerization of unsaturated fatty alcohols, in the form of their sodium salts. Additional examples are the sulphation products of the adducts of 1 to 10 moles ethylene oxide on the mentioned alcohols, also in the form of their sodium salts. Especially preferable is the use of sodium lauryl sulphate.

Monoglyceride (Ether) Sulphates

Monoglyceride sulphates and monoglyceride ether sulphates, which also are of interest as component (a), are likewise known anionic surfactants, which can be obtained according to the usual methods of the preparative organic chemistry. Normally triglycerides are used for their preparation, which where appropriate after ethoxylation are transesterified to the monoglycerides and thereafter sulphated and neutralized. It is also possible to react the partial glycerides with suitable sulphating agents, preferably gaseous sulphur trioxide or chlorosulfonic acid [see EP-B1 0561825, EP-B1 0561999 (Henkel)]. The monoglyceride (ether) sulphates which can be used according to the invention preferably have the formula (II),

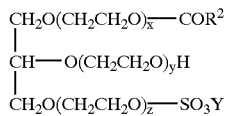

where $R^2CO$ represents a linear or branched acyl residue with 6 to 22 carbon atoms, x, y and z represent in total 0 or the numbers 1 to 30, preferably 2 to 10, and Y represents an alkali or alkaline earth metal. Typical examples of suitable monoglyceride (ether) sulphates according to the invantion are the reaction products of lauric acid monoglyceride, coco fatty acid monoglyceride, palmitic acid monoglyceride, stearic acid monoglyceride, oleic acid monoglyceride and tallow fatty acid monoglyceride, as well as their ethylene oxide adducts with sulphur trioxide or chlorosulfonic acid in the form of their sodium salts. Preferably the monoglyceride sulphates of the formula (II) are used, where RICO represents a linear acyl residue with 8 to 18 carbon atoms.

Alkyl and/or Alkenyl Oligoglycosides

Alkyl- and alkenyl oligoglycosides, which also can be used as components (a) are known nonionic surfactants, with the formula (III),

wherein $R^3$ represents an alkyl and/or alkenyl residue with 4 to 22 carbon atoms, G represents a sugar residue with 5 or 6 carbon atoms and page represents numbers from 1 to 10. They can be obtained according to the usual methods of the preparative organic chemistry. Instead of the extensive literature, reference is made to the survey of Biermann et al. in *Starch/Stärke* 45, 281 (1993), B. Salka in *Cosm. Toil.* 108,89 (1993) as well as J. Kahre et al. in *SÖFW-Journal*, issue 8, 598 (1995). The alkyl and/or alkenyl oligoglycosides can be derived from aldoses or ketoses with 5 or 6 carbon atoms, preferably glucose. The preferred alkyl and/or alkenyl oligoglycosides are therefore alkyl and/or alkenyl oligoglucosides. The index number p i the general formula (II) states the degree of oligomerization (DP), that is the distribution of mono-and oligoglycosides and represents a number between 1 and 10. Whilst p in a given compound always has to be an integer and here first of all can take the values p=1 to 6, the value p for a specific alkyl oligoglycoside is an analytically determined calculated value, which usually is a fractional number. Preferably used are alkyl and/or alkenyl oligoglycosides with an average degree of oligomerization p from 1,1 to 3,0. From the standpoint of application technology such alkyl and/or alkenyl oligoglycosides are preferred, which degree of oligomerization is less than 1.7 and especially between 1.2 and 1.4. The alkyl, respectively the alkenyl, residue $R^3$ can be derived from primary alcohols with 4 to 11, preferably 8 to 10 carbon atoms. Typical examples are butanol, capron alcohol, capryl alcohol, caprin alcohol and undecyl alcohol as well as their technical mixtures, such as obtained for example by the hydrogenation of fatty acid methyl esters of technical quality or during the hydrogenation of aldehyds from Roeten's oxo synthesis. Preferred are alkyl oligoglucosides having chain lengths of C8–C10(DP=1 to 3), which are accumulated by the destillative separation of technical C8–C10 coco fatty alcohol and which can be contaminated with less than 6% by weight of C12 alcohol as well as alkyl oligoglucosides based on technical $C_{9/11}$ oxo alcohols (DP=1 to 3). The alkyl, respectively the alkenyl, residue $R^3$ can further be obtained from primary alcohols with 12 to 22, preferably 12 to 14, carbon atoms. Typical examples are lauryl alcohol, myristyl alcohol, cetyl alcohol, palmoleyl alkohof, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their technical mixtures, which can be obtained as described above. Alkyl oligoglucosides based on hardened C12/14 coco alcohol with a DP of 1 to 3 are preferred.

Water Soluble β-(1,3) Glucans

The term glucans is intended to mean homopolysaccharides based on glucose. Depending on sterical linking there is a difference between β-(1,3), β-(1,4) and β-(1,6) glucans. β-(1,3) Glucans normally show a helical structure, whereas glucans with a (1,4) linkage generally have a linear structure. The β-glucans of the invention have a (1,3) structure, i.e. they are substantillay free from undesired (1,6) linkages. Preferably such β-(1,3) glucans are used where the side chains exclusively show (1,3) linkages. Especially the agents contain glucans which are obtained on the basis of yeast from the family Sacchaomyces, especially *Saccharomyces cerevisiae*. Glucans of this type are available in technical amounts according to known methods. The international patent application WO 95/30022 (Biotec-Mackzymal) describes e.g. a method for producing such substances, wherein glucans with β-(1,3) and β-(1,6) linkages are brought in contact with β-(1,6) glucanases in such a way, that practically all β-(1,6) linkages are loosened. Preferably used for the manufacture of these glucans are glucanases based on *Trichodermia harzianum*. As to the manufacture and availability of the glucans contained in these agents, reference is made to the above cited publication. Preferably the weight ratio of surfactants and glucans in the mixtures lies in the range of 100:1 to 10:1 and preferably 90:1 to 50:1.

Chitosan and Chitosan Derivatives

In a preferable embodiment of the invention the surfactants and glucans can be used together with chitosans and/or chitosan derivatives (component c). Chitosans are biopolymers and belong to the group of hydrocolloids. From a chemical point of view they are partial deacetylated chitins with different molecular weights, and contain the following—idealized—monomer module:

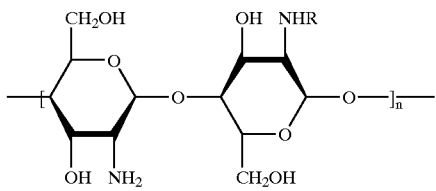

In contrast to most of the hydrocolloids, which are negatively charged in the range of biological pH-values, chitosans are under these conditions cationic biopolymers. The positively charged chitosans can interact with opposite charged surfaces and are therefore used in cosmetic hair and body care agents as well as in pharmaceutical preparations (see *Ullmann's Encyclopedia of Industrial Chemistry*, 5th Ed., vol. A6, Weinheim, Verlag Chemie, 1986, p. 231–332). A summary of these subjects are also published in for example B. Gesslein et al., *HAPPI* 27, 57 (1990), O. Skaugrud in *Drug Cosm. Ind.* 148, 24 (1991) and E. Onsoyen et al. in *Seifen-Öle-Fette-Wachse* 117, 633 (1991). By the production of chitosan chitin is used as starting material, preferably the shell residues of crust animals, which are available in large amounts as cheap raw materials. The chitin is thereby, using a method which first was described by Hackmann et al., usually first deprotonated by addition of bases, demineralized by addition of mineral acids and at last deacetylated by addition of strong bases, whereby the molecular weights can be distributed over a broad spectrum. Corresponding methods are for example known from *Makromol. Chem.* 177, 3589 (1976) or the French patent application FR-A1 2701266. Preferably use is made of such types which are described in the German patent applications DE-A1 4442987 and DE-A1 19537001 (Henkel), and which have an average molecular weight of 10 000 to 2 500 000, preferably 800 000 to 1 200 000 Daltons, a viscosity according to Brookfield (1% by weight in glycolic acid) below 5 000 mPas, a degree of deacetylation in the range of 80 to 88% and a content of ashes of less than 0.3% by weight. In addition to the chitosanes as typical cationic biopolymers come according to the invention also in question anionic, respectively nonionic derivatized chitosans, such as e.g. carboxylation, succinilation or alkoxylation products, as they are described for example in the German patent DE-C2 3713099 (L'Oreal) as well as in the German patent application DE-A1 19604180 (Henkel). These are characterised through an especially good compatibility with other surfactants.

Auxiliary and Additive Substances

The preparations which can be obtained through the use according to the invention of the surface active mixtures can as grinding and polishing agents contain chalk, dicalcium phosphate, insoluble sodium metaphosphate, aluminum silicate, layered silicates, hydrotalcite, calcium pyrophosphate, finely divided synthetic resins, silicic acids, aluminum oxide, aluminum oxide trihydrate, talcum, zeolites, magnesium aluminum silicate (Veegum®), calcium sulphate, magnesium carbonate and/or magnesium oxide. In addition as further auxiliary and additive substances finally aroma components can be used, for example peppermint oil, crisped mint oil, anise oil, star-anise oil, caraway oil, eucalyptus oil, fennel, cinnamon oil, carnation oil, geranium oil, sage oil, pimento oil, thyme oil, marjoram oil, basil oil, citrus oil, gaultheria oil or one or more therefrom isolated or synthetically made components of these oils, such as menthol, carvon, anethol, cineol, eugenol, cinnamon aldehyde, cargophyllen, geraniol, citronellol, linalool, salvoes, thymol, terpinan, terpinol, methyl chavicol and methyl salicylate. Additional suitable aromas are methyl acetate, vanillin, ionone, linalyl acetate, rhodinol and piperiton. Suitable sweetening agents are either natural sugars as sucrose, maltose, lactose and fructose or synthetic sweetening agents as saccharin sodium salt, sodium cyclamate or aspartame. Further suitable for the use especially in toothpastes as auxiliary and additional substances are moisturizing agents such as sorbitol or glycerol, substances which give consistency, deodorizing active agents, agents active against mouth and tooth diseases, water soluble fluorine compounds such as sodium fluoride or sodium monofluoro phosphate. The amount of the auxiliary and additional substances is not critical and depends on the type of the finished agent. Usually the amount will be 5 to 98 and preferably 80 to 90% by weight, based on the agents. Typical tooth pastes, which constitute an additional object of the invention, usually exhibit the following composition.

(a) 1 to 10, preferably 2 to 8% by weight of anionic and/or nonionic surfactants, (b) 0.1 to 2, preferably 0.5 to 1% by weight of water soluble β-(1,3) glucans, which are substantially free from β-(1,6) linkages, (c) 0 to 2, preferably 0.1 to 1% by weight of chitosan, respectively chitosan derivatives, (d) 1 to 25, preferably 10 to 20% by weight of grinding and polishing agents, (e) 0 to 65, preferably 10 to 30% by weight of moisturizing agents, (f) 0 to 3, preferably 1 to 2% by weight of aroma substances, and (g) 0 to 5, preferably 1 to 3% by weight of additional auxiliaries, provided that the used amounts with water summarize to 100% by weight.

EXAMPLES

The surfactant mixtures were worked into a standard tooth paste formulation. The foaming properties were determined according to the rub foam method (Reibschaummethode) in a EHMEDA rub foam apparatus [Fette, Seifen, Anstrichmitt. 66 955 (1964)]. For this purpose 20 grams of tooth paste were dispersed in 180 grams of water and heated in the foam cylinder to 45° C. Therein foam was made through 60 seconds rubbing with a vertical rotating perlon brush at 2600 rev. per min. on a metal wire grid having cylindrical form. In Table 1 the foam volume after 0.5 min. and 5 min. after the end of the foam formation as well as that after 5 min. from the foam separated drainage water is specified. The assessment of the stability took place in a subjective manner after storage for 4 weeks at 400° C.; (+) means stable, homogeneous distribution of the abrasive materials; (−) agglomeration and (− −) sedimentation. The estimation of taste followed after brushing of teeth by 5 independent test persons according to the following criteria: (+ +)=aroma predominant, no aftertaste; (+)=slight aftertaste; (−)= intensive aftertaste. The examples 1 to 4 in Table 1 are according to the invention, the examples V1 to V3 are for comparison.

TABLE 1

Evaluation of tooth pastes
(amounts as % by weight)

| Composition/ performance | 1 | 2 | 3 | 4 | V1 | V2 | V3 |
|---|---|---|---|---|---|---|---|
| Sodium lauryl sulphate | 2.0 | — | 2.0 | — | 2.0 | — | 2.0 |
| Sodium glyceryl cocoate sulphate | — | 2.0 | — | 2.0 | — | 2.0 | — |
| Coco glucosides | — | — | 0.5 | 1.0 | — | — | — |
| Betaglucans* | 0.1 | 0.1 | 0.1 | 0.1 | — | — | — |
| Chitosan** | — | — | 0.1 | 0.1 | — | — | 0.1 |
| Silica gel | 22.0 | 22.0 | 22.0 | 22.0 | 22.0 | 22.0 | 22.0 |
| Sodium carboxymethyl cellulose | 1.2 | 1.2 | 1.2 | 1.2 | 1.2 | 1.2 | 1.2 |
| Saccharin, sodium salt | 0.1 | 0.1 | 0.1 | 0.1 | 0.1 | 0.1 | 0.1 |
| Sodium benzoate | 0.1 | 0.1 | 0.1 | 0.1 | 0.1 | 0.1 | 0.1 |
| Sodium fluoride | 0.2 | 0.2 | 0.2 | 0.2 | 0.2 | 0.2 | 0.2 |
| Sorbitol (70% by weight) | 15.0 | 15.0 | 15.0 | 15.0 | 15.0 | 15.0 | 15.0 |
| Glycerol (86% by weight) | 25.0 | 25.0 | 25.0 | 25.0 | 25.0 | 25.0 | 25.0 |
| Flavour | 3.0 | 3.0 | 3.0 | 3.0 | 3.0 | 3.0 | 3.0 |
| Water | | | | ad 100 | | | |
| Rub foam [ml] | | | | | | | |
| after 0.5 min. | 780 | 810 | 820 | 830 | 740 | 760 | 780 |
| after 5 min. | 600 | 610 | 610 | 640 | 530 | 530 | 520 |
| Drainage water | 60 | 55 | 55 | 60 | 70 | 65 | 75 |
| Stability | + | + | + | + | − − | − | − |
| Taste evaluation | + | + | + | + + | − | + | + |

*Highcareen ® GS,
**Hydagen ® CMF (both Henkel KGaA, Düsseldorf/FRG)

What is claimed is:

1. In the method of preparing compositions for oral hygiene and dental hygiene products, the improvement comprising the addition of surface active mixtures containing (a) anionic and/or nonionic surfactants and
(b) water soluble branched β-(1,3) glucans, with side chains having β-(1,3) linkages and which are substantially free of β-(1,6) linkages,
   to the composition for oral hygiene and dental hygiene products.

2. The method according to claim 1, wherein as component (a) anionic surfactants are used which are chosen from the group consisting of alkyl sulphates, alky ether sulphates, monoglyceride (ether) sulphates and olefine sulphates.

3. The method according to claim 1, wherein as component (a) nonionic surfactants of the type alkyl and/or alkenyl oligoglycosides are used.

4. The method according to claim 1, wherein as component (b) water soluble β-(1,3) glucans are used which are obtained based on yeasts from the family Saccharomyces.

5. The method according to claim 4, wherein glucans are used which are obtained by contacting glucans with β-(1,3) and β-(1,6) linkages with β-(1,6) glucanases in such a way that practically all β-(1,6) linkages are loosened.

6. The method according to claim 5, wherein glucans are us, which previously have been treated with glucanases based on *Trichodermia harzianum*.

7. The method according to claim 1, wherein the surfactants and the glucans are used in weight ratios 100:1 to 10:1.

8. The method according to claim 1, wherein as further component (c) chitosans are used.

9. The method according to claim 1, wherein the oral hygiene or dental hygiene products include toothpaste, tooth gels, mouth paste, mouth wash and chewing gums.

10. A toothpaste composition comprising:
    (a) 1 to 10% by weight of anionic and/or nonionic surfactants,
    (b) 0.1 to 2% by weight of water soluble branched β-(1,3) glucans, with side chains having β-(1,3,) linkages and which are substantially free from β-(1,6) linkages,
    (c) 0.1 to 2% by weight of chitosan,
    (d) 1 to 25% by weight of grinding and polishing agents,
    (e) 0 to 65% by weight of moisturizing agents,
    (f) 0 to 3% by weight of aroma substances, and
    (g) 0 to 5% by weight of additional auxiliaries,
    provided that the used amounts with water summarize to 100% by weight.

11. The method according to claim 1, wherein oral hygiene and dental hygiene products are selected from the group consisting of mouthwash, chewing gums, toothpastes and tooth gels.

* * * * *